(12) United States Patent
Arafati et al.

(10) Patent No.: US 11,651,487 B2
(45) Date of Patent: May 16, 2023

(54) FULLY AUTOMATED FOUR-CHAMBER SEGMENTATION OF ECHOCARDIOGRAMS

(71) Applicant: THE REGENTS OF THE UNIVERSITY OF CALIFORNIA, Oakland, CA (US)

(72) Inventors: Arghavan Arafati, Brookline, MA (US); Hamid Jafarkhani, Irvine, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 411 days.

(21) Appl. No.: 16/926,517

(22) Filed: Jul. 10, 2020

(65) Prior Publication Data

US 2021/0012885 A1    Jan. 14, 2021

Related U.S. Application Data

(60) Provisional application No. 62/873,766, filed on Jul. 12, 2019.

(51) Int. Cl.
*G06T 7/00* (2017.01)
*G06N 3/04* (2006.01)
*G06N 3/08* (2006.01)
*G06T 7/174* (2017.01)
*G16H 30/40* (2018.01)
(Continued)

(52) U.S. Cl.
CPC ......... *G06T 7/0012* (2013.01); *G06N 3/0454* (2013.01); *G06N 3/088* (2013.01); *G06T 7/174* (2017.01); *G06N 3/084* (2013.01); *G06T 2207/10132* (2013.01);
(Continued)

(58) Field of Classification Search
CPC .............. G06T 7/0012; G06T 7/174; G06T 2207/10132; G06T 2207/20084; G06T 2207/30048; G06N 3/0454; G06N 3/088; G06N 3/0481; G06N 3/0472; G06N 3/084; G16H 30/40
See application file for complete search history.

(56) References Cited

FOREIGN PATENT DOCUMENTS

WO    WO-2018136805 A1 * 7/2018 ............. A61B 6/503

OTHER PUBLICATIONS

Tran, P.H., "A Fully Convolutional Neural Network for Cardiac Segmentation in Short-Axis MRI," arXiv, 2014, p. 1-21, https://arxiv.org/abs/1604.00494 (Year: 2014).*

(Continued)

*Primary Examiner* — Nay A Maung
*Assistant Examiner* — Daniella M. DiGuglielmo
(74) *Attorney, Agent, or Firm* — Perkins Coie LLP

(57) ABSTRACT

Devices, systems and methods related to techniques for performing four-chamber segmentation of echocardiograms are disclosed. In one example aspect, a method for generating segmented image data based on an input echocardiogram includes receiving an input echocardiogram that includes information associated with four chambers of a heart, performing segmentation on the information associated with the four chambers using an adversarial model that comprises a first artificial neural network with multiple layers, and combining data from selected layers of the first artificial neural network to generate an output image that includes the segmented four chambers of the heart.

18 Claims, 15 Drawing Sheets

(51) Int. Cl.
G06N 3/088 (2023.01)
G06N 3/084 (2023.01)
(52) U.S. Cl.
CPC ............. G06T 2207/20084 (2013.01); G06T 2207/30048 (2013.01); G16H 30/40 (2018.01)

(56) References Cited

OTHER PUBLICATIONS

Zhang J, Gajjala S, Agrawal P, Tison GH, Hallock LA, Beussink-Nelson L, Lassen MH, Fan E, Aras MA, Jordan C, Fleischmann KE, Melisko M, Qasim A, Shah SJ, Bajcsy R, Deo RC. Fully Automated Echocardiogram Interpretation in Clinical Practice. Circulation. Oct. 16, 2018;138(16):1623-1635. (Year: 2018).*
Madani, A., Ong, J.R., Tibrewal, A. et al. Deep echocardiography: data-efficient supervised and semi-supervised deep learning towards automated diagnosis of cardiac disease, npj Digital Med 1, 59 (2018). https://doi.org/10.1038/s41746-018-0065-x (Year: 2018).*
Avendi, M.R., Kheradvar, A., Jafarkhani, H. A combined deep-learning and deformable-model approach to fully automatic segmentation of the left ventricle in cardiac MRI. Medical Image Analsyis. 2016;20:108-119. https://doi.org/10.1016/j.media.2016.01.005 (Year: 2016).*
Arafati, Arghavan, et al., "Fully Automated 4-Chamber Segmentation of Echocardiograms using Deep Learning," University of California, Irvine (41 pages).
Ahmad, E., Goyal, M., McPhee, J.S., Degens, H., Yap, M.H., 2018. Semantic Segmentation of Human Thigh Quadriceps Muscle in Magnetic Resonance Images.
Avendi, M., Kheradvar, A., Jafarkhani, H., 2016. A combined deep-learning and deformable-model approach to fully automatic segmentation of the left ventricle in cardiac MRI. Medical Image Analysis 30, 108-119.
Avendi, M.R., Kheradvar, A., Jafarkhani, H., 2017. Automatic Segmentation of the Right Ventricle from Cardiac MRI Using a Learning-based Approach. Magn Reson Med in press.
Barbosa, D., Dietenbeck, T., Schaerer, J., D'hooge, J., Friboulet, D., Bernard, O., 2012. B-spline explicit active surfaces: an efficient framework for real-time 3-D region-based segmentation. IEEE Transactions on Image Processing 21, 241-251.
Belous, G., Busch, A., Rowlands, D., 2013. Segmentation of the Left Ventricle from Ultrasound Using Random Forest with Active Shape Model, 2013 1st International Conference on Artificial Intelligence, Modelling and Simulation, pp. 315-319.
Bland, J.M., Altman, D., 1986. Statistical methods for assessing agreement between two methods of clinical measurement. The Lancet 327, 307-310.
Boureau, Y.-L., Ponce, J., LeCun, Y., 2010. A theoretical analysis of feature pooling in visual Yecognition, Proceedings of the 27th International Conference on Machine Learning (ICML-10), pp. 111-118.
Carneiro, G., Nascimento, J.C., 2013. Combining multiple dynamic models and deep learning architectures for tracking the left ventricle endocardium in ultrasound data. IEEE Transactions on Pattern Analysis and Machine Intelligence 99, 1.
Carneiro, G., Nascimento, J.C., Freitas, A., 2012. The Segmentation of the Left Ventricle of the Heart From Ultrasound Data Using Deep Learning Architectures and Derivative-Based Search Methods. IEEE Transactions on Image Processing 21, 968-982.
Carneiro, G., Zheng, Y., Xing, F., Yang, L., 2017. Review of deep learning methods in mammography, cardiovascular, and microscopy image analysis, Deep Learning and Convolutional Neural Networks for Medical Image Computing. Springer, pp. 11-32.
Chen, H., et al., "Iterative multi-domain regularized deep learning for anatomical structure detection and segmentation from ultrasound images", Int'l Conference on Medical Image Computing and Computer-Assisted Intervention. Springer, pp. 487-495, 2016.
Cobzas, D., Schmidt, M., 2009. Increased discrimination in level set methods with embedded conditional random fields, Computer Vision and Pattern Recognition, 2009. CVPR 2009. IEEE Conference on. IEEE, pp. 328-335.
Cordero-Grande, L., et al., "Unsupervised 4D myocardium segmentation with a Markov Random Field based deformable model," Medical Image Analysis 15, 283-301, 2011.
Dai, W., et al., SCAN: Structure correcting adversarial network fororgan segmentation in chest X-rays, Deep Learning in Medical Image Analysis and Multimodal Learning for Clinical Decision Support. Springer, pp. 263-273, 2018.
De Geer, L., Oscarsson, A., Engvall, J., 2015. Variability in echocardiographic measurements of left ventricular function in septic shock patients. Cardiovascular ultrasound 13, 19.
Dreijer, J.F., Herbst, B.M., Du Preez, J.A., 2013. Left ventricular segmentation from MRI datasets with edge modelling conditional random fields. BMC Med Imaging 13, 24.
Furiasse, N., Thomas, J.D., 2015. Automated Algorithmic Software in Echocardiography Artificial Intelligence?*. Journal of the American College of Cardiology 66, 1467-1469.
Georgescu, B., Zhou, X.S., Comaniciu, D., Gupta, A., 2005. Database-guided segmentation of anatomical structures with complex appearance, Computer Vision and Pattern Recognition, 2005. CVPR 2005. IEEE Computer Society Conference on. IEEE, pp. 429-436.
Geremia, E., Clatz, O., Menze, B.H., Konukoglu, E., Criminisi, A., Ayache, N., 2011. Spatial decision forests for MS lesion segmentation in multi-channel magnetic resonance images. Neuroimage 57, 378-390.
Glorot, X., Bengio, Y., 2010. Understanding the difficulty of training deep feedforward neural networks, Proceedings of the thirteenth international conference on artificial intelligence and statistics, pp. 249-256.
Haak, Alexander, et al., "Segmentation of multiple heart cavities in 3-D transesophageal ultrasound images," IEEE transactions on ultrasonics, ferroelectrics, and frequency control 62, 1179-1189, 2015.
Hajiaghayi, M., Groves, E.M., Jafarkhani, H., Kheradvar, A., 2017. A 3-D Active Contour Method for Automated Segmentation of the Left Ventricle From Magnetic Resonance Images. IEEE Transactions on Biomedical Engineering 64, 134-144.
Hoffmann, Rainer, et al., "Analysis of interinstitutional observer agreement in interpretation of dobutamine stress echocardiograms," Journal of the American College of Cardiology 27, 330-336, 1996.
Huang, Rui, et al., "Agraphical model framework for coupling MRFs and deformable models," Computer Vision and Pattern Recognition, 2004. CVPR 2004. Proceedings of the 2004 IEEE Computer Society Conference on. IEEE, pp. 739-746, vol. 732.
Jia, Yangqing, et al., "Caffe: Convolutional architecture for fast feature embedding," Proceedings of the 22nd ACM international conference on Multimedia. ACM, pp. 675-678, 2014.
Karpathy, A., 2016. Cs231n: Convolutional neural networks for visual recognition. Neural Networks 1.
Knackstedt, Christian, et al., "Fully automated versus standard tracking of left ventricular ejection fraction and longitudinal strain: the FAST-EFs Multicenter Study," J Am Coll Cardiol 66, 1456-1466, 2015.
Lahiri, A., et al., "Generative Adversarial Learning for Reducing Manual Annotation in Semantic Segmentation on Large Scale Miscroscopy Images: Automated Vessel Segmentation in Retinal Fundus Image as Test Case", 2017, p. 794-800.
Lang, R.M., Recommendations for cardiac chamber quantification by echocardiography in adults: an update from the American Society of Echocardiography and the European Association of Cardiovascular Imaging. Europ Heart J-Cardiovas Img 16, 233-271, 2015.
Lempitsky, V., Verhoek, M., Noble, J.A., Blake, A., 2009. Random forest classification for automatic delineation of myocardium in real-time 3D echocardiography, Functional Imaging and Modeling of the Heart. Springer, pp. 447-456.
Li, C., Wand, M., 2016. Precomputed real-time texture synthesis with markovian generative adversarial networks, European Conference on Computer Vision. Springer, pp. 702-716.
Lin, N., Yu, W., Duncan, J.S., 2003. Combinative multi-scale level set framework for echocardiographic image segmentation. Medical Image Analysis 7, 529-537.

(56) References Cited

OTHER PUBLICATIONS

Litjens, G., Kooi, T., Bejnordi, B.E., Setio, A.A.A., Ciompi, F., Ghafoorian, M., van der Laak, J.A.W.M., van Ginneken, B., Sánchez, C.I., A survey on deep learning in medical image analysis. Medical Image Analysis 42, 60-88.

Long, J., Shelhamer, E., Darrell, T., 2015. Fully convolutional networks for semantic segmentation, Proceedings of the IEEE Conference on Computer Vision and Pattern Recognition, pp. 3431-3440.

Luo, G., An, R., Wang, K., Dong, S., Zhang, H., 2016. A Deep Learning Network for Right Ventricle Segmentation in Short:Axis MRI.

Margeta, J., et al., "Layered spatio-temporal forests for left ventricle segmentation from 4D cardiac MRI data", Statistical Atlases and Computational Models of the Heart. Imaging and Modelling Challenges. Springer, pp. 109-119, 2012.

Marsousi, M., et al., "Endocardial boundary extraction in left ventricular echocardiographic images using fast and adaptive B-spline snake algorithm," International Journal of Computer Assisted Radiology and Surgery 5, 501-513, 2010.

Mirza, M., Osindero, S., 2014. Conditional generative adversarial nets.

Mortazi, A., Burt, J., Bagci, U., 2017a. Multi-Planar Deep Segmentation Networks for Cardiac Substructures from MRI and CT.

Mortazi, A., et al., "CardiacNET: Segmentation of Left Atrium and Proximal Pulmonary Veins from MRI Using Multi-View CNN," International Conference on Medical Image Computing and Computer-Assisted Intervention. Springer, pp. 377-385, 2017.

Nascimento, J.C., Marques, J.S., 2008. Robust shape tracking with multiple models in ultrasound images. IEEE Transactions on Image Processing 17, 392-406.

Ngo, T.A., et al., "Fully Automated Non-rigid Segmentation with Distance Regularized Level Set Evolution Initialized and Constrained by Deep-structured Inference", Computer Vision and Pattern Recognition (CVPR), 2014 IEEE Conf on IEEE, pp. 3118-3125, 2014.

Noble, J.A., Boukerroui, D., 2006. Ultrasound image segmentation: a survey. IEEE Transactions on Medical Imaging 25, 987-1010.

Parisi, A., Moynihan, P., Feldman, C., Folland, E., 1979. Approaches to determination of left ventricular volume and ejection fraction by real-time two-dimensional echocardiography. Clinical cardiology 2, 257-263.

Peng, P., et al., "A review of heart chamber segmentation for structural and functional analysis using cardiac magnetic resonance imaging," Magnetic Resonance Materials in Physics, Biology and Medicine 29, 155-195, 2016.

Petitjean, C., Dacher, J.-N., 2011. A review of segmentation methods in short axis cardiac MR images. Medical Image Analysis 15, 169-184.

Pietro, D.A., Voelkel, A.G., Ray, B.J., Parisi, A.F., Reproducibility of Echocardiography. Chest 79, 29-32.

Pinedo, M., et al., "Inter-and intra-observer variability in the echocardiographic evaluation of right ventricular function," Revista Española de Cardiología (English Edition) 63, 802-809, 2010.

Poudel, R.P., Lamata, P., Montana, G., 2016. Recurrent fully convolutional neural networks for multi-slice MRI cardiac segmentation, Reconstruction, Segmentation, and Analysis of Medical Images. Springer, pp. 83-94.

Qin, X., Cong, Z., Fei, B., 2013. Automatic segmentation of right ventricular ultrasound images using sparse matrix transform and a level set. Physics in Medicine & Biology 58, 7609.

Radau, P., Lu, Y., Connelly, K., Paul, G., Dick, A., Wright, G., 2009. Evaluation framework for algorithms segmenting short axis cardiac MRI. The MIDAS Journal-Cardiac MR Left Ventricle Segmentation Challenge 49.

Radford, A., Metz, L., Chintala, S., 2015. Unsupervised representation learning with deep convolutional generative adversarial networks. arXiv preprint arXiv:1511.06434.

Rezaei, M., Harmuth, K., Gierke, W., Kellermeier, T., Fischer, M., Yang, H., Meinel.C., 2017. A Conditional Adversarial Network for Semantic Segmentation of Brain Tumor, International MICCAI Brainlesion Workshop. Springer, pp. 241-252.

Simonyan, K., Zisserman, A., 2014. Very deep convolutional networks for large-scale image recognition. arXiv preprint arXiv:1409.1556.

Smistad, E., Østvik, A., 2017. 2D left ventricle segmentation using deep learning, Ultrasonics Symposium (IUS), 2017 IEEE International. IEEE, pp. 1-4.

Son, J., Park, S.J., Jung, K.-H., 2017. Retinal vessel segmentation in fundoscopic images with generative adversarial networks. arXiv preprint arXiv:1706.09318.

Tajbakhsh, N., Shin, J.Y., Gurudu, S.R., Hurst, R.T., Kendall, C.B., Gotway, M.B., Liang, J., 2016. Convolutional neural networks for medical image analysis: full training or fine tuning? IEEE Transactions on Medical Imaging 35, 1299-1312.

Thorstensen, A., Dalen, H., Amundsen, B.H., Aase, S.A., Stoylen, A.,2010. Reproducibility in echocardiographic assessment of the left ventricular global and regional function, the HUNT study. European Journal of Echocardiography 11, 149-156.

Xue, Y., Xu, T., Zhang, H., Long, L.R., Huang, X., 2018. Segan: Adversarial network with multi-scale I 1 loss for medical image segmentation. Neuroinformatics, 1-10.

Yi, X., Walia, E., Babyn, P., 2018. Generative adversarial network in medical imaging: A review. arXiv preprint arXiv:1809.07294.

\* cited by examiner

FULLY AUTOMATED FOUR-CHAMBER SEGMENTATION OF ECHOCARDIOGRAMS

CROSS-REFERENCE TO RELATED APPLICATIONS

This application claims priority to U.S. Provisional Patent Application No. 62/873,766, titled "FULLY AUTOMATED FOUR-CHAMBER SEGMENTATION OF ECHOCARDIOGRAMS," filed on Jul. 12, 2019. The entire disclosure of the aforementioned application is incorporated by reference as part of the disclosure of this application.

TECHNICAL FIELD

This patent document relates to automated segmentation of echocardiograms.

BACKGROUND

Two-dimensional echocardiography is the most commonly used noninvasive imaging tool to study cardiac structures and function. Thus, accurate segmentation of the heart chambers is the stepping stone for objective evaluation of the cardiac function. However, manual segmentation of echocardiograms leads to significant intra- and inter-operator variability.

SUMMARY

Devices, systems and methods related to techniques for performing four-chamber segmentation of echocardiograms are disclosed.

One aspect of the disclosed technology relates to a method for generating segmented image data based on an input echocardiogram. The method includes receiving an input echocardiogram that includes information associated with four chambers of a heart, performing segmentation on the information associated with the four chambers using an adversarial model that comprises a first artificial neural network with multiple layers, and combining data from selected layers of the first artificial neural network to generate an output image that includes the segmented four chambers of the heart.

Another example aspect of the disclosed technology relates to a device for processing an input echocardiogram. The device includes a processor, and a memory including processor executable code. The processor executable code upon execution by the processor configures the processor to receive an input echocardiogram that includes information associated with four chambers of a heart, perform segmentation on the information associated with the four chambers using an adversarial model that comprises a first artificial neural network with multiple layers, and combine data from selected layers of the first artificial neural network to generate an output image that includes the segmented four chambers of the heart.

In yet another example aspect, a system for segmenting echocardiogram images includes a first artificial neural network configured to receive an input echocardiogram that includes information associated with four chambers of a heart. The first artificial neural network is configured to perform segmentation on the information associated with the four chambers based on generating data representative of an intermediate image that is smaller than the input echocardiogram, modifying the data representative of the intermediate image, and generating one or more probability maps based on the data representative of the intermediate image. Modifying the data representative results in at least one of: randomly displacing a center of the intermediate image, zooming up the intermediate image, distorting a mean or a standard deviation of pixel values in the intermediate image, rotating the intermediate image, or adding noise to the intermediate image. Each of the one or more probability maps indicating a likelihood of a pixel being present in at least one of the four chambers. The system also includes a second artificial neural network in communication with the first artificial neural network to receive the one or more probability maps and to determine whether a segmented chamber corresponds to a manually performed segmentation of the chamber.

DETAILED DESCRIPTION

Figure 1:
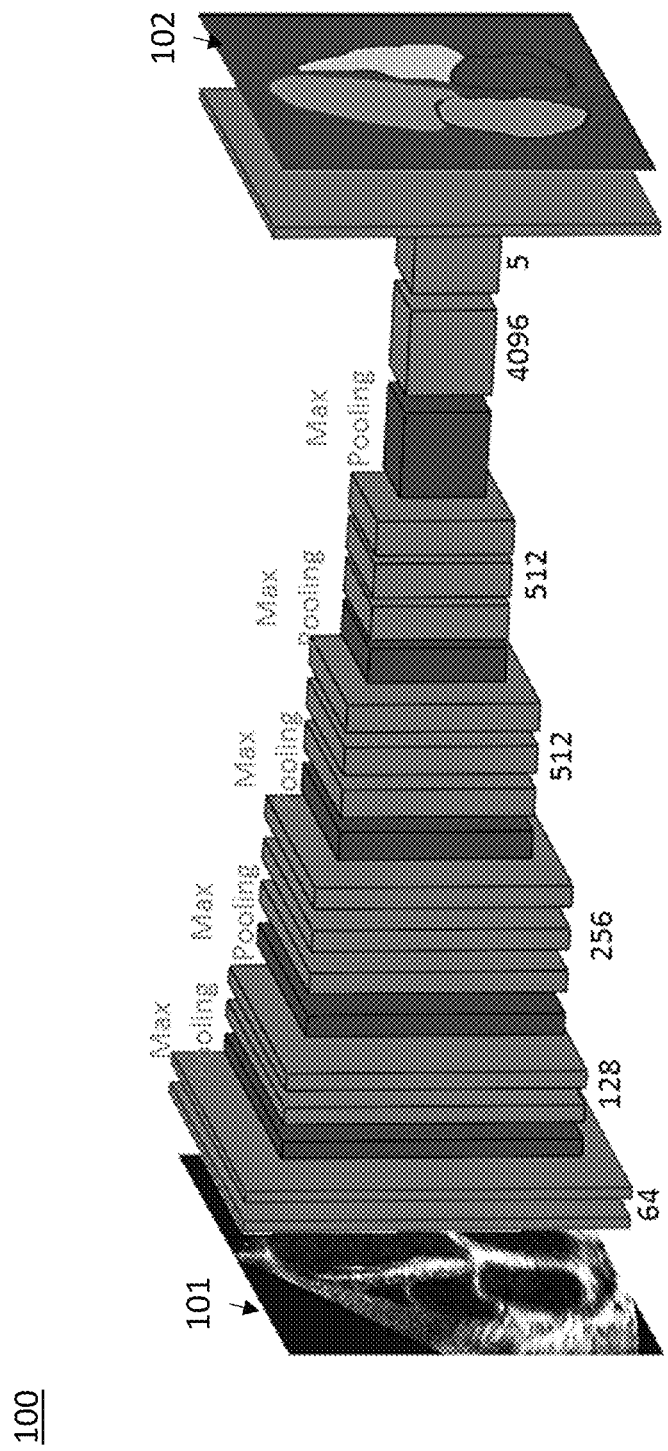
FIG. 1 illustrates an example architecture of a four-chamber segmentation network in accordance with the present technology.

Echocardiography has become the preferred imaging modality to study the heart chambers for routine screening purposes due to its portability, real-time application, and overall cost. However, it suffers from subjective interpretation and inter- and intra-observer variability. Three-dimensional (3D) echocardiography has been instrumental for many cardiac applications such as valvular heart disease. However, in many places, the imaging laboratory workflow depends on two-dimensional (2D) echocardiography. Nevertheless, interpretation of 2D echocardiography has yet remained unsatisfactory, with chambers' volumes commonly calculated by subjective manual chamber segmentation. The clinical need for accurate and automated analysis of echocardiograms is currently unmet and goes back many years. Despite remarkable advancement in the quality of echocardiograms, inhomogeneity in intensity, edge dropout and low signal-to-noise ratio impede the use of automatic segmentation for accurate, clinically-acceptable chambers' volume calculation.

Previous attempts to automate cardiac segmentation were mainly focused on left ventricle (LV) due to the emerging needs for assessment of left heart function. However, recent attentions to the significance of other chambers, e.g., right ventricle (RV) and left atrium (LA) in progression of the heart disease, and in particular, structural heart problems, necessitate approaches for quantification of multiple heart chambers.

Active contours, deformable models, and supervised learning methods have been the most popular automatic and semi-automatic techniques commonly used for segmentation of echocardiograms. The first two methods suffer from contour shrinkage and leakage problems, particularly in low-quality images and small heart chambers. Intensity inhomogeneity, edge dropout and low signal to noise ratio have made the automatic segmentation of echocardiograms a challenging task. Further, the need for prior knowledge about the reference heart chamber shapes made these techniques less attractive for multi-chamber fully automatic segmentation.

In recent years, learning-based approaches have received significant attention to mitigate the tedious conventional methods in medical image segmentation, particularly for cardiac imaging. In particular, the number of learning algorithms for cardiac Magnetic Resonance Imaging (MRI) segmentation has been dramatically increased, due to existing publicly-available datasets as grand challenges. For example, convolutional neural networks (CNNs) can be used to build hierarchies of features. CNNs are similar to ordinary artificial neural networks and are composed of convolutional layers that filter (convolve) the inputs with learnable parameters (kernel) so that these filters are automatically adjusted to extract the most useful information for the task without feature selection. CNN's main advantage is the explicit assumption that the inputs are images, which allows encoding certain properties into the architecture. CNNs make the forward function and optimization process more efficient to implement by reducing the number of parameters in the network. A Fully Convolutional Neural Network (FCN) is a normal CNN, except that the fully connected layers are converted to one or more convolution layers with a large "receptive field." FCNs aim to capture the rough estimation of the locations of elements and overall context in the image. FCNs can efficiently be trained end-to-end, pixels-to-pixels for tasks like semantic segmentation. The training process is performed by dense feedforward and backpropagation computations. Generally, pixel or voxel-wise loss such as cross entropy has been commonly used for segmentation.

Although recent FCNs with skip connections can combine both the low- and high-level features, spatial consistency in the final segmentation map cannot be assured. Alternatively, adversarial training can consider the high order potentials. More recently, attention has been given to leveraging the advancements in Generative Adversarial Networks (GANs) to improve medical image segmentation for different body organs. A GAN is designed to have a segmentor block and a critic network as the discriminator. The discriminator can be regarded as a shape regulator, which affects the internal features of the segmentor to achieve domain invariance.

Contrary to the everyday use of echocardiograms, only limited studies have been conducted for their segmentation. Given the limited number of studies involving echocardiograms and the relatively-poor segmentation results compared to cardiac MRI, an accurate learning-based segmentation technique has the potential to transform echocardiographic-based diagnostic imaging by eliminating the inter- and intra-operator variability. This is a clinical unmet need since the clinical indices calculated by different operators are not readily comparable. The disclosed techniques herein can be implemented to develop a fully automated four-chamber segmentation system for echocardiograms. The disclosed techniques are suitable for 2D echocardiograms but can also be extended to 3D echocardiograms. Using the techniques disclosed herein, the segmentation of echocardiograms can be performed in-part by employing an adversarial model including FCNs for fully automated segmentation of the heart's all four chambers.

Figure 2:
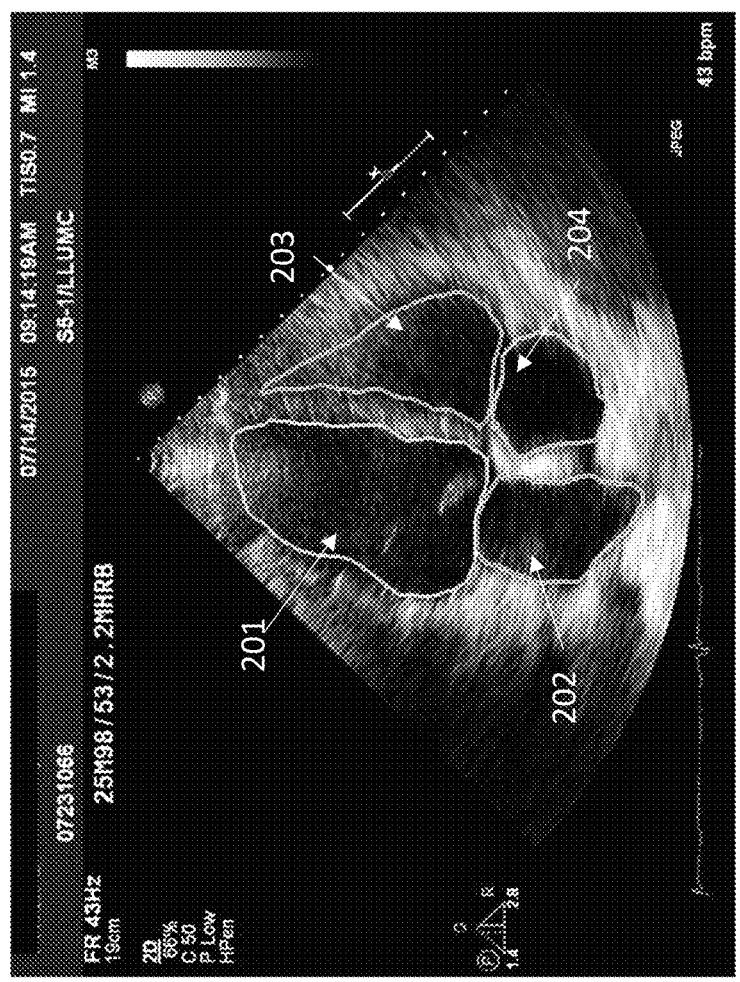
FIG. 2 illustrates an example of a manually segmented image.

FIG. 1 illustrates an example architecture of a four-chamber segmentation network 100 in accordance with the present technology. The network receives an input echocardiogram 101 that includes four chambers of a heart as part of a noisy image and can produce an output image 102 showing segmentations of the four chambers. In some embodiments, a dataset of echocardiograms (e.g., over 1000 images) can be partitioned into two sets: a training set and a test set. For example, one example dataset of 1395 annotated images from 100 normal subjects was used. The study population in this particular dataset includes 73 women and 27 men, with a mean age of 36.45±13.55. For images in the test set, manual segmentations can be performed by a board-certified cardiologist for selected frames (e.g., one in every five frames) of the cardiac cycle as well as the end diastolic (ED) and end systolic (ES) images for each subject. FIG. 2 illustrates an example of a manually segmented image.

Referring back to FIG. 1, the network 100 includes convolution in the fully connected structure in different stride sizes in the deconvolution layers. In some embodiments, 32-pixel and 8-pixel stride sizes are used. For example, for FCN-8s, the model's final output was a product of upsampling of the third pooling layer, upsampling of the fourth pooling layer multiplied by two, and upsampling of the seventh convolutional layer multiplied by four, which showed improved performance for object segmentation.

The example deep neural network as shown in FIG. 1 can require a considerable amount of data to be effectively trained. However, the size of the database can be limited because patient data may not be readily available. To address the challenge of training data size, transfer learning and/or fine-tuning can be used to improve results given a small dataset of echocardiograms. For example, in place of random initialization for the network parameters, transfer learning that uses the weights from pre-trained models can be applied first. The new dataset can then be used to fine-tune the network. In some embodiments, the weights associated with the pre-trained models can be used to subsequently fine-tune the deep learning algorithm.

In some embodiments, a softmax classification layer can be used to generate the probability map. In some embodiments, the entire network can be trained via a mini-batch gradient descent method by minimizing a pixel-wise cross-entropy (multinomial logistic) loss function on the 4-chamber echocardiograms dataset. For example, the following equations can be implemented to achieve this objective:

$$\hat{p}_{nk} = \frac{\exp(x_{nk})}{[\Sigma_{k'} \exp(x_{nk'})]}, \forall n \sum_{k=1}^{K} \hat{p}_{nk} = 1 \qquad \text{Eq. (1)}$$

$$E_{seg} = \frac{-1}{N} \sum_{n=1}^{N} \sum_{k=1}^{K} l_{nk} \log(\hat{p}_{nk}) + \frac{\lambda}{2} \sum_{n=1}^{N} \|W_n\|^2 \qquad \text{Eq. (2)}$$

where $x_{nk} \in [-\infty, +\infty]$ is the predicted score for each k=1, 2, ..., 5 classes for each node n=1, 2, ..., N, $\hat{p}_{nk}$ represents softmax output class probabilities, and $l_{nk} \in [0,1]$ indicates the correct class label probability among the five classes, including the heart's 4-chambers and the background $$\frac{\lambda}{2} \sum_{n=1}^{N} \|W_n\|^2$$

is the regularization term, which penalizes large values of the weights matrix $W_n$. ($\lambda=10^{-9}$)

In some embodiments, the network can be fine-tuned for roughly 90 epochs through the training set. The training process can be performed only once.

In some embodiments, the original size of the images was 600×800, which can be down-sampled to 300×400 and cropped to 256×256 pixels as input for the example architecture 100 as shown in FIG. 1. To improve invariance and robustness properties in training process of the network with limited number of training images, real-time data augmentation can be performed by randomly displacing the image's center point up to 30 pixels, zooming up to ±15%, shear distorting the mean and standard deviation (SD) up to ±0.15, rotating up to 30 degree, and/or adding Gaussian noise with 0.15 SD. The network's outputs then can be probability map for each pixel.

Figure 3:
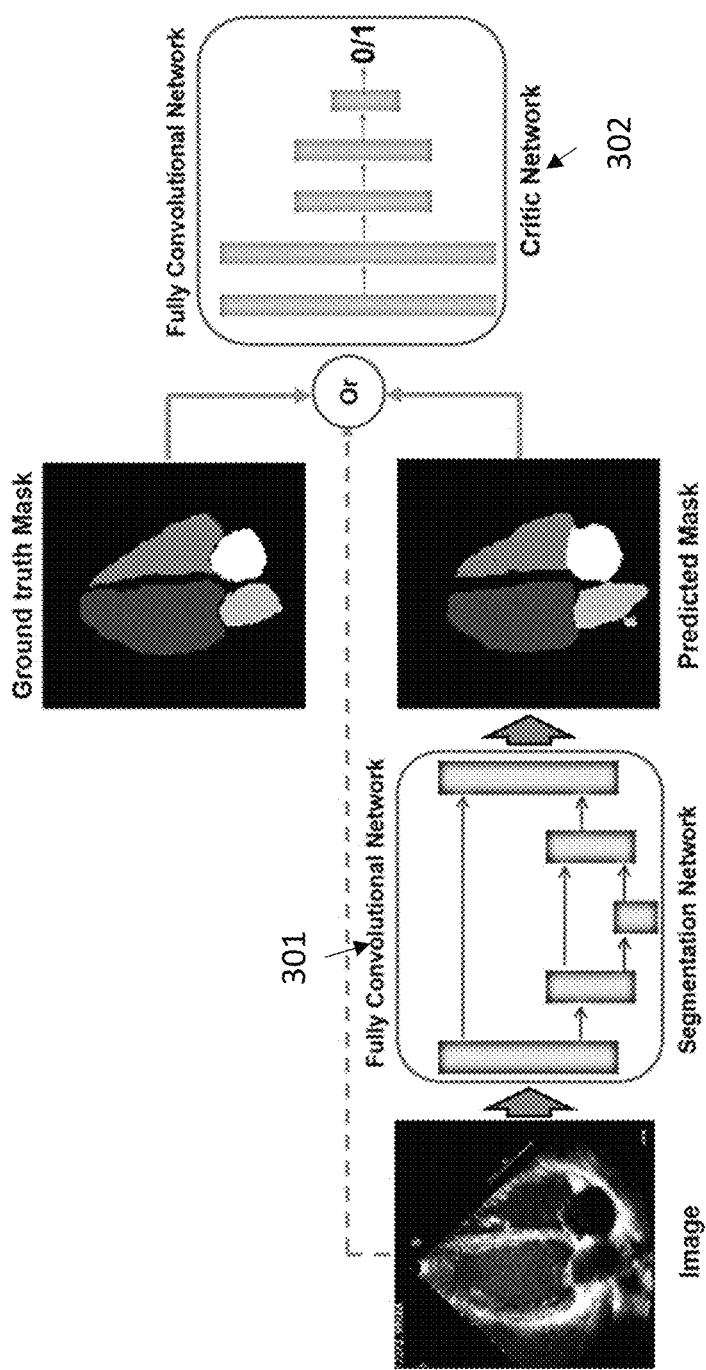
FIG. 3 is a schematic diagram illustrating an example Generative Adversarial Networks (GANs) framework for echocardiogram segmentation in accordance with the present technology.

FIG. 3 is a schematic diagram illustrating an example Generative Adversarial Networks (GANs) framework for echocardiogram segmentation in accordance with the present technology. In some embodiments, a generator (segmentor) 301 is given an echocardiogram to generate probability maps for all four chambers with the same size as the input. Values in the probability maps range from 0 to 4 indicating the probability of a pixel being present in each chamber or in the background. The discriminator 302 takes an echocardiogram and the segmentation map to determine whether the segmented image is the ground truth drawn by the human expert or output of the generator. For the generator, initial convolutional feature maps can be skip-connected to up-sampled layers from the bottleneck layers. The GAN's cost function can be developed as:

$$L_{GAN} = E_{x,y \sim p_{data}(x,y)}[\log D(x,y)] + E_{x \sim p_{data}(x)}[\log(1 - D(x, G(x)))] \qquad \text{Eq. (3)}$$

where generator G x→y and discriminator D: {x, y}→[0,1] where 0 and 1 means that y is either machine-generated or human annotated, respectively. In the training process, the generator can prevent the discriminator from making correct judgment by producing outputs that are undetectable from the real data. So, D(x, y) can be maximized while D(x, G(x)) can be minimized. Since the ultimate goal is to obtain realistic outputs from the generator, the objective function can be defined as the objective's mini-max.

A categorical cross entropy loss function can be added for segmentation task $E_{seg}$ (e.g., Eq. (2)) to have additional penalty for the difference between ground truth and generated labels. Thus, the final loss function can be formulated as:

$$G^* = \arg \min_G [\max_D L_{GAN}(G, D) + \lambda E_{Seg}(G)] \qquad \text{Eq. (4)}$$

Wherein $\lambda$ is a Lagrange multiplier to balance the two objective functions.

Figure 4:
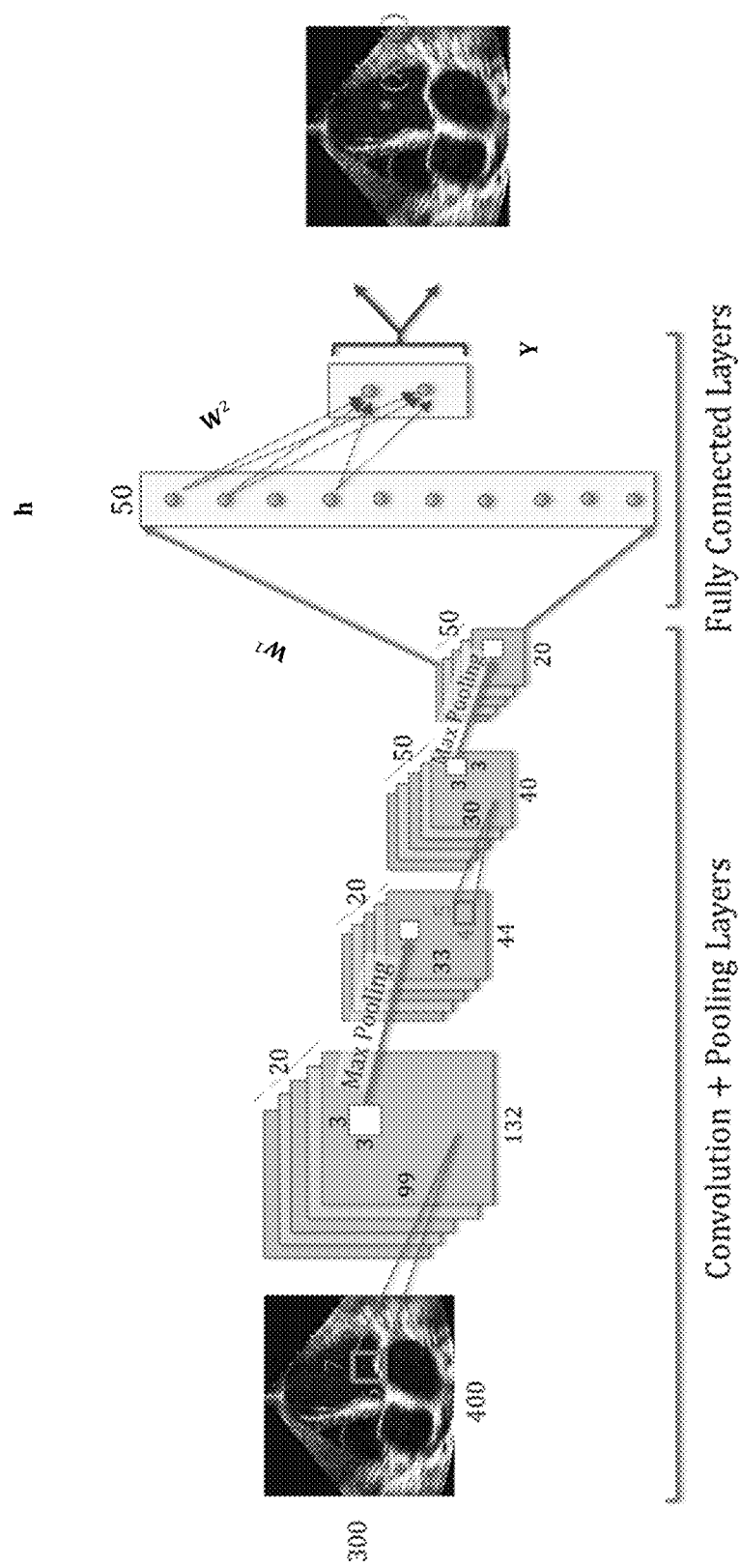
FIG. 4 illustrates an example process of localizing left ventricle (LV) and region of interest (ROI) in accordance with the present technology.
Figure 15:
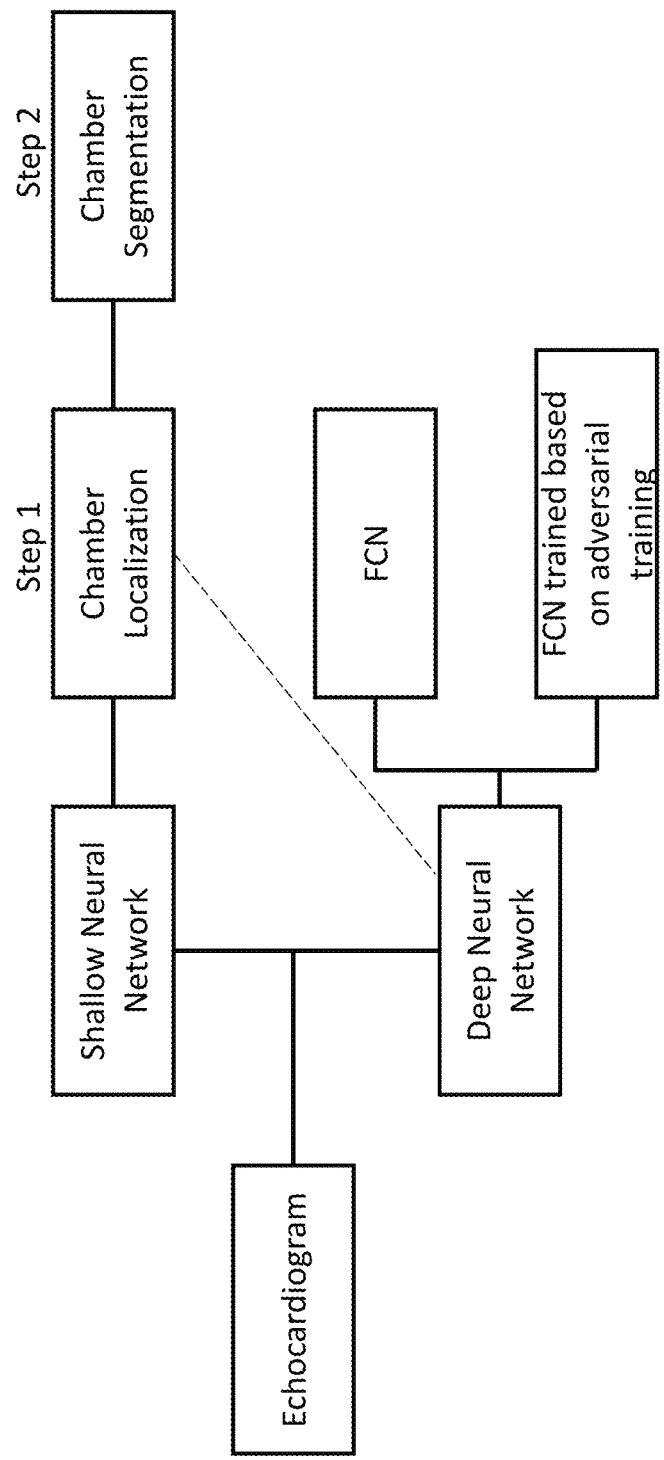
FIG. 15 illustrates an example overview of using a deep network for simultaneous four-chamber segmentation and/or a shallow network for a two-step segmentation of a single chamber in accordance with the present technology.

The 4-chamber echocardiogram, as shown in FIG. 2, includes all four chambers of the heart 201, 202, 203 and 204. Alternatively, or in addition, to reduce the computational complexity and time, and to improve the procedural accuracy, a two-step segmentation process can be used. FIG. 15 illustrates an example overview of using a deep network for simultaneous four-chamber segmentation and/or a shallow network for a two-step segmentation of a single chamber in accordance with the present technology. The two-step algorithm's first step is to locate the LV chamber and compute a Region Of Interest (ROI) around it. FIG. 4 illustrates an example process of localizing LV and ROI in accordance with the present technology. To perform LV localization, filters $F\_1 \in R^{(6 \times 7)}$, $b\^0 \in R\^20$ can be convolved with the input image to obtain the convolved feature maps. The convolved features can be computed as $C\_1 [i,j] = f(Z\_1 [i,j])$ where:

$$Z_l[i,j] = \Sigma_{k_1=1}^{6} \Sigma_{k_2=1}^{7} F_l[k_1, k_2] I[i+k_1-1, j+k_2-1] + b^0[l] \qquad \text{Eq. (5)}$$

where $1 \leq i \leq 99$, $1 \leq j \leq 132$ and $l=1, \ldots, 20$. This resulted in 20 convolved features $Z_l \in \mathbb{R}^{99 \times 132}$. Next, the convolved feature maps can be sub-sampled using max pooling and the maximum over non-overlapping blocks with size 3×3 can be computed in each feature map for $1 \leq i_1 \leq 33$, $1 \leq j_1 \leq 44$ as:

$$P_l[i_1, j_1] = \max \left\{ \begin{array}{l} C_l[i, j]: i = (3i_1 - 2), (3i_1 - 1), 3i_1 \\ j = (3j_1 - 2), (3j_1 - 1), 3j_1 \end{array} \right\} \qquad \text{Eq. (6)}$$

Accordingly, twenty reduced-resolution feature maps $P_l \in \mathbb{R}^{33 \times 44}$ for $l=1, \ldots, 20$ can be achieved. In some embodiments, those feature maps are followed by a similar mechanism including convolution and pooling layers such that 50 convolved features $Z'_l \in \mathbb{R}^{30 \times 40}$ are pooled to lower resolution feature maps as $P'_l \in \mathbb{R}^{15 \times 20}$ for $l=1, \ldots, 50$. Finally, the pooled features can be unrolled as vector $p \in \mathbb{R}^{300}$ and fully connected to an inner product hidden layer with 50 outputs, followed by a linear regression layer with 2 outputs specifying the coordinates of the center point. Thus, the last two layers computed: $h = f(W^1 p + b^1)$, and $Y = f(W^2 h + b^2)$, where $W^1 \in \mathbb{R}^{50 \times 300}$, $b^1 \in \mathbb{R}^{50}$, $W^2 \in \mathbb{R}^{2 \times 50}$ and $b^2 \in \mathbb{R}^2$ are trainable matrices.

Training the convolution network includes obtaining the optimal values of filters $F_l$, $l=1, \ldots, 20$, $F'_l$, $l=1, \ldots, 50$ as well as the other parameters: $b^0$, $W^2$ and $b^2$. Filters can be randomly initialized using Xavier method and simultaneously constructed during the training process. The whole network can then be optimized by minimizing the cost function, J, using the backpropagation algorithm:

$$J(F, W, b) = \frac{1}{2}\sum_{i=1}^{N=2} |Y^{(i)} - Y_c^{(i)}|^2 + \quad \text{Eq. (7)}$$

$$\frac{\lambda}{2}\left(\|W^1\|^2 + \|W^2\|^2 + \sum_{l=1}^{20} \|F_l\|^2 + \sum_{l'=1}^{50} \|F'_{l'}\|^2\right)$$

with $\Delta=10^{-4}$. For further processing in the next steps, the center of the LV chamber can be subsequently computed and used to crop a ROI of size 156×105 from the original image. To find the LV contour, a 4-fully connected layer neural network is trained with 2 hidden layers.

Figure 5:
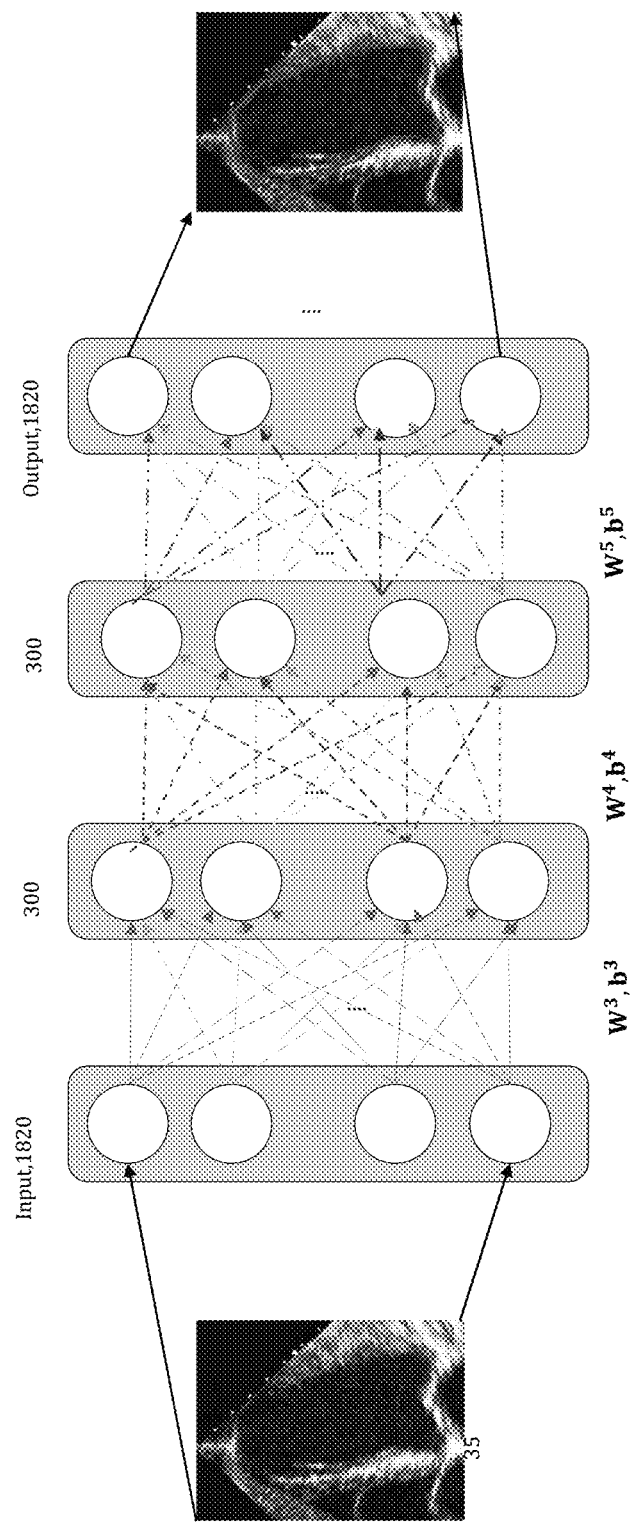
FIG. 5 illustrates an example process of segmenting the LV in accordance with the present technology.

In some embodiments, the identified ROI of the LV chamber can be provided to the GAN to assist simultaneous segmentation of the four chambers. In some embodiments, the two-step algorithm proceeds to the second step of segmenting the LV chamber. FIG. 5 illustrates an example process of segmenting the LV in accordance with the present technology. The sub-image obtained from the previous block was sub-sampled and unrolled as vector $x \in \mathbb{R}^{1820}$ and fed into the input layer. Two inner product hidden layers with 300 outputs, followed by a linear regression layer with 1820 outputs specify the LV mask. Accordingly, the layers compute $h^3=f(W^3p+b^3)$, $h^4=f(W^4h^3+b^4)$, and $Y_{LV}=f(W^5h^4+b^{5'})$, where $W^3 \in \mathbb{R}^{300 \times 1820}$, $b^3 \in \mathbb{R}^{300}$, $W^4 \in \mathbb{R}^{300 \times 300}$, $b^4 \in \mathbb{R}^{300}$, $W^5 \in \mathbb{R}^{1820 \times 300}$ and $b^5 \in \mathbb{R}^{1820}$ are trainable matrices. Next, a cost function including Euclidean loss and regularization term as follows can be minimized using the back-propagation algorithm with respect to the supervised criterion to train the network, in which $Y_{LV}^{(i)} \in \mathbb{R}^{1820}$ is the ground truth mask corresponding to the $i^{th}$ image. The labeled data are binary masks created from the manual segmentations drawn by the expert and cropped from 4-chamber labels ($\lambda=10^{-4}$).

$$J_2(W, b) = \quad \text{Eq. (8)}$$

$$\frac{1}{2N_2}\sum_{i=1}^{N_2} |Y_{ROI}^{(i)} - Y_{LV}^{(i)}|^2 + \frac{\lambda}{2}(\|W^3\|^2 + \|W^4\|^2 + \|W^5\|^2)$$

After identifying the LV center, original images can be cropped to 260×175 pixels and down-sampled by a factor of 0.2 to reduce the complexity of segmentation phase. In the next step, the images can be normalized so that the gray-value be in the range of [0.1, 0.9], consistent with the network's sigmoid activation function. To avoid overfitting, in this phase, the training dataset can be enlarged using the techniques previously discussed. Accordingly, the training dataset is augmented a factor of N>0 (e.g., N=5).

To test the models' performance, segmented images (from test dataset) can be compared and measured with the corresponding ground truth (i.e., manually annotations by the expert). Haussdorf distance, sensitivity, specificity, and Dice Similarity Coefficient (DSC) can be used for evaluation of segmented chambers. Furthermore, segmented chambers' area can be calculated in $cm^2$, based on automatic and manual segmentation results and used for comparison in terms of correlation and Bland-Altman analyses. The correlation analysis can be performed using the Pearson's test to obtain the slope, intercept equation and the R-values. To assess the intra- and inter-observer variability, the coefficient of variation (CV), defined as the standard deviation (SD) of the differences between the automatic and manual results divided by their mean values, and the reproducibility coefficient (RPC), defined as 1.96*SD, can be computed.

Considering the importance of the LV volume and the fact that 2D echocardiograms are still more popular in clinical routine, various estimation methods have been used for LV volume calculation based on 2D echocardiograms. However, the disclosed techniques can be applied to 3D echocardiography data as it is desirable to perform accurate volume measurement using 3D data sets. Using the output data generated using the techniques disclosed herein, an ellipsoid model can calculate LV volume as a function of area (A) and apical length (l) based on four-chamber long axis view:

$$V = \frac{8A^2}{3\pi l} \quad \text{Eq. (9)}$$

Figure 6:
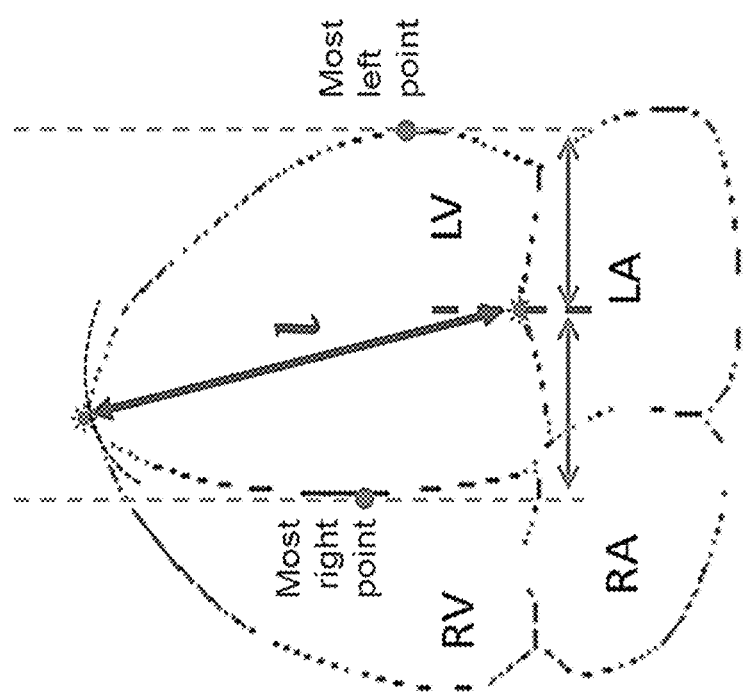
FIG. 6 illustrates an example of computing the LV volume in accordance with the present technology.

FIG. 6 illustrates an example of computing the LV volume in accordance with the present technology. As shown in FIG. 6, apical lengths (l) for end-diastolic and end-systolic frames can be calculated automatically by connecting the LV apex to the midline of the mitral valve where the LV apex is designated as the furthest point to the mitral valve. According to manual measurements performed, the difference between automatically-calculated and manually-measured lengths is 2.0%±1.9. Accordingly, the LV volumes can be calculated fully automatically based on Eq. (9).

Figure 7:
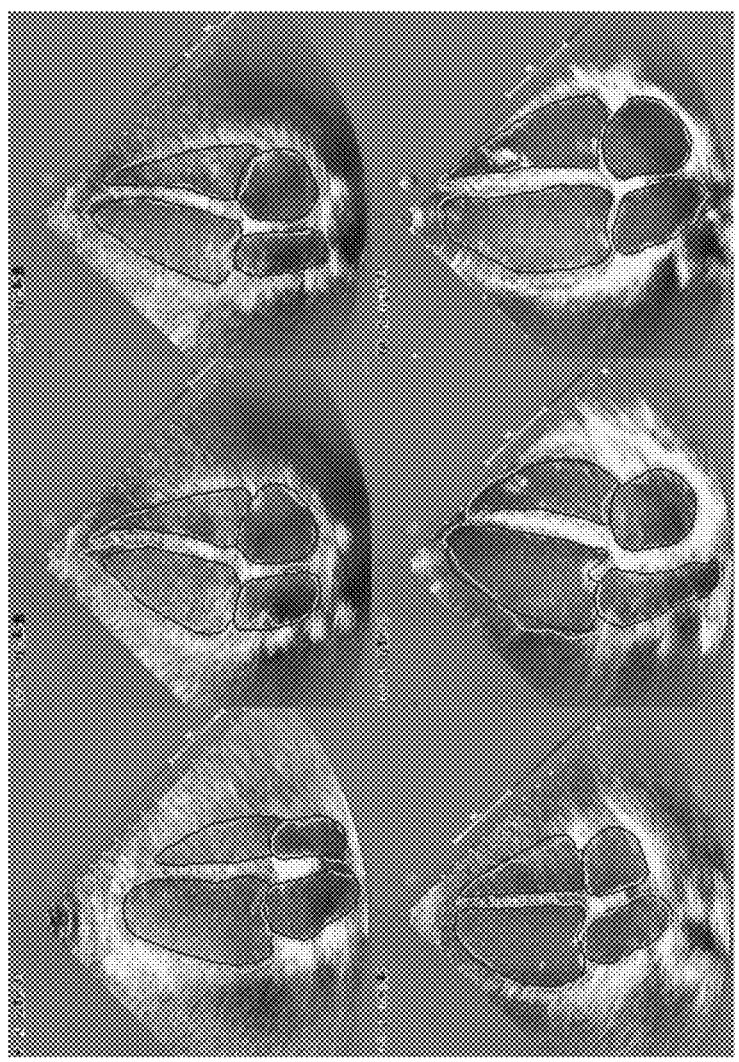
FIG. 7 illustrates example results of automatic and manual segmentation of all four chambers.

FIG. 7 illustrates example results of automatic and manual segmentation of all four chambers. The automatically segmented areas are indicated using the black contour lines, which are very close to the manually segmented areas indicated using the grey contour lines.

Instead of complementary image processing methods, here, the accuracy of segmentation approach can be improved by employing adversarial training technique to pixel classification. Table 1 shows example metrics in terms of average values and standard variation obtained from 449 images of 30 subjects. In Table 1, Mod-FCN-VGG stands for modified FCN in accordance with the present technology. Post processing includes cleaning the masks and/or filling the holes.

As shown in Table 1, applying adversarial training combined with FCNs for pixel classification can improve results by an additional 1% compared to the use of FCNs alone, and 3% compared to shallow fully-connected network for LV. Using the similar adversarial training led to 5%, 2% and 3% improvement in the average dice metric for RV, LA and RA, respectively.

TABLE 1

Example evaluation metrics obtained from 449 images of 30 subjects

| | | Dice (%) | HD (mm) |
|---|---|---|---|
| Left Ventricle | CNN + Fully Connected Net | 89.15 ± 4.5 | 14.1 |
| | Mod-FCN-VGG32s | 88.32 ± 4.0 | 13.4 |
| | Mod-FCN-VGG8s | 91.35 ± 3.7 | 12.12 |
| | FCN + Adversarial Training | 92.04 ± 3.4 | 5.81 |
| | FCN + Adversarial Training + Post processing | 92.13 ± 3.3 | 5.19 |
| Right Ventricle | Mod-FCN-VGG32s | 81.69 ± 8.5 | 15.2 |
| | Mod-FCN-VGG8s | 84.96 ± 7.7 | 17.4 |
| | FCN + Adversarial Training | 86.25 ± 9.7 | 7.91 |
| | FCN + Adversarial Training + Post processing | 86.26 ± 9.7 | 7.86 |
| Left Atrium | Mod-FCN-VGG32s | 87.14 ± 6.2 | 10.1 |
| | Mod-FCN-VGG8s | 89.72 ± 5.8 | 9.8 |

TABLE 1-continued

Example evaluation metrics obtained from 449 images of 30 subjects

| | | Dice (%) | HD (mm) |
|---|---|---|---|
| | FCN + Adversarial Training | 89.43 ± 6.7 | 5.34 |
| | FCN + Adversarial Training + Post processing | 89.62 ± 6.6 | 5.20 |
| Right Atrium | Mod-FCN-VGG32s | 88.19 ± 4.5 | 11.4 |
| | Mod-FCN-VGG8s | 91.01 ± 4.4 | 10.6 |
| | FCN + Adversarial Training | 91.30 ± 4.7 | 5.10 |
| | FCN + Adversarial Training + Post processing | 91.45 ± 4.4 | 4.86 |

Table 2 shows example comparison of the techniques disclosed here and the state-of-the-art methods for echocardiograms.

TABLE 2

Example Comparison of Different Techniques

| | | Dice (%) | HD (mm) | Method | # of images | # of subjects |
|---|---|---|---|---|---|---|
| Left Ventricle | (Marsousi et al., 2010) | 91.13 ± 4.96 | — | ACM | 50 | NA |
| | (Chen etal., 2016) | 87.9 | — | Learning | 3,118 | NA |
| | (Carneiro and Nascimento, 2013) | 90.7 | — | Learning + Dynamic Model | 132 | NA |
| | (Belous etal., 2013) | 90.09 ± 0.03 | 16.04 ± 6.38 | Learning + ASM | NA | 35 |
| | (Smistad and Ostvik, 2017) | 87.0 ± 6 | 5.9 ± 2.9 | Learning | 52 | 13 |
| | FCN + Adversarial Training + Post processing | 92.13 ± 3.3 | 5.19 ± 7.6 | Adversarial Training | 449 | 30 |
| Right Ventricle | (Qin et al., 2013) | 87.3 ± 1.9 | 7.02 ± 1.17 | matrix transform + level set | 1,158 RV focused | NA |
| | FCN + Adversarial Training + Post processing | 86.26 ± 9.7 | 7.86 ± 14.0 | Adversarial Training | 449 | 30 |
| Left Atrium | FCN + Adversarial Training + Post processing | 89.62 ± 6.6 | 5.20 ± 11.4 | Adversarial Training | 449 | 30 |
| Right Atrium | FCN + Adversarial Training + Post processing | 91.45 ± 4.4 | 4.86 ± 12.4 | Adversarial Training | 449 | 30 |

Table 3 compares example sensitivity and specificity of the disclosed techniques for each heart chamber.

TABLE 3

Example Sensitivity and Specificity

| | Chamber | Sensitivity (%) | Specificity (%) |
|---|---|---|---|
| | LV | 92.59 | 99.30 |
| Adversarial training + FCN | RV | 86.17 | 99.41 |
| | LA | 90.91 | 99.64 |
| | RA | 92.23 | 99.63 |

Figure 8:
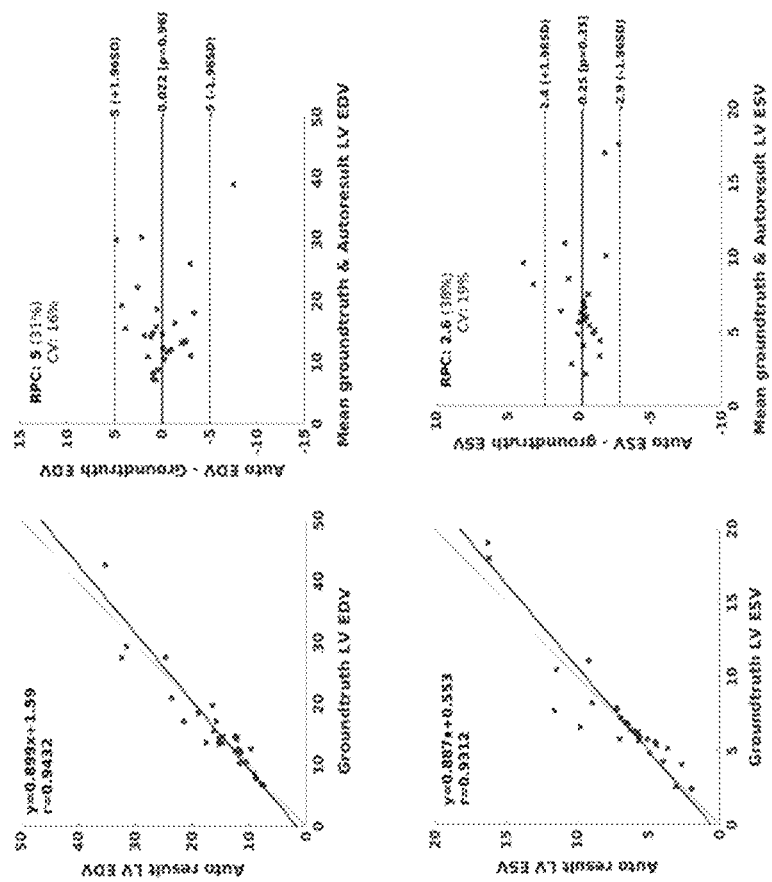
FIG. 8 illustrates example correlation graphs and Bland-Altman plots for LV end-diastolic volume (EDV) and LV end-systolic volume (ESV).

FIG. 8 illustrates example correlation graphs and Bland-Altman plots for LV end-diastolic volume (EDV) and LV end-systolic volume (ESV). Correlation for volumes calculated based on ground truth contours with the ones calculated based on automatic segmentation is 0.94 and 0.93 for EDV and ESV, respectively.

Figure 9:
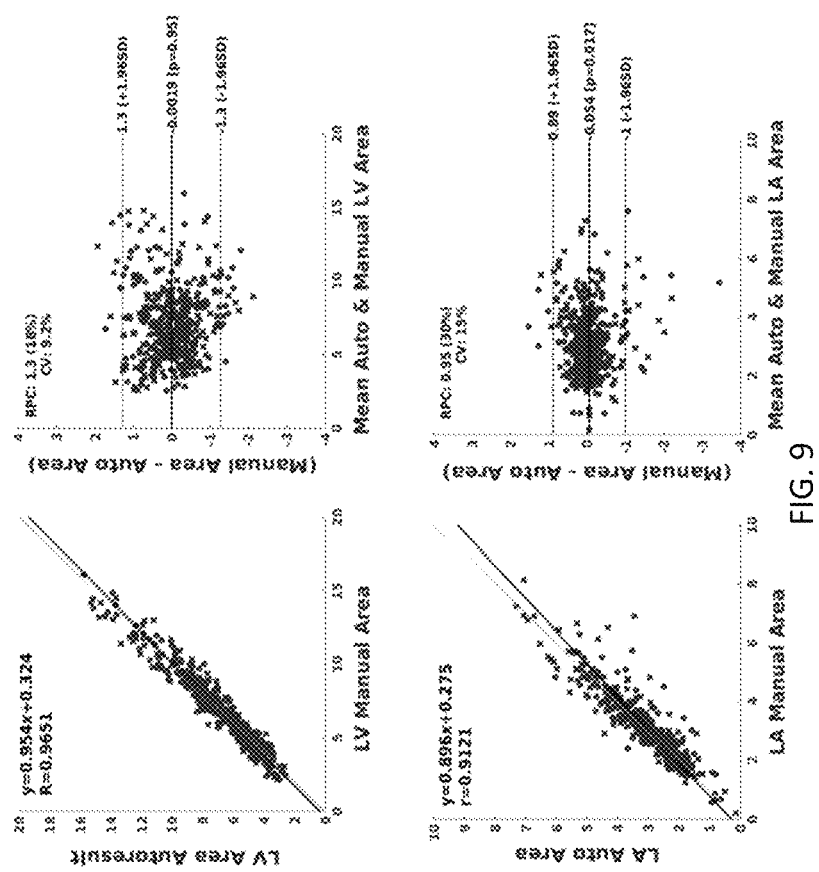
FIG. 9 illustrates example correlation graphs and Bland-Altman graphs between the automatic and manual areas related to all four chambers.
Figure 10:
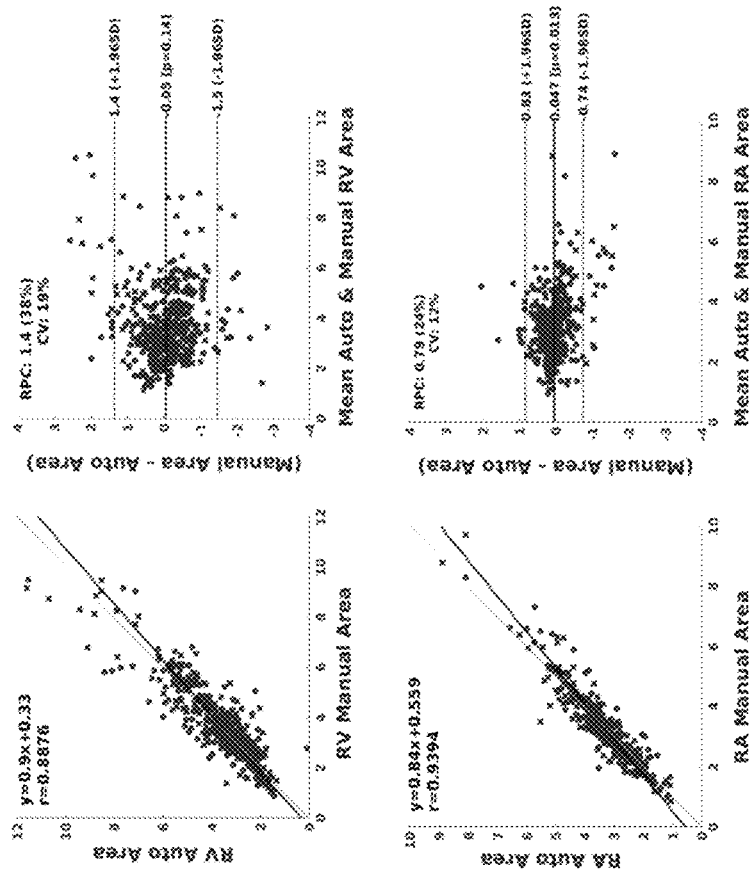
FIG. 10 illustrate another set of example correlation graphs and Bland-Altman graphs between the automatic and manual areas related to all four chambers.
Figure 11:
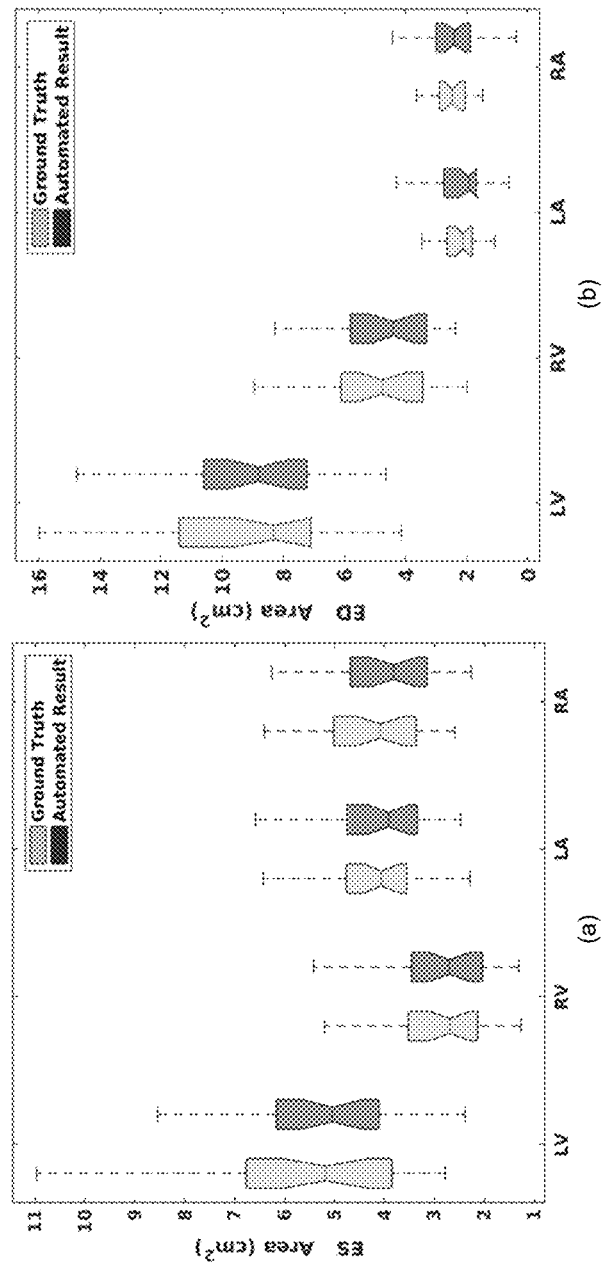
FIG. 11 shows example box-plots for end-systolic and end-diastolic areas for all four chambers.

FIG. 9 and FIG. 10 illustrate example correlation graphs and Bland-Altman graphs between the automatic and manual areas related to all four chambers. Correlation with the ground truth contours of 0.96, 0.89, 0.91 and 0.94 were achieved for LV, RV, LA and RA, respectively. The level of agreement between the automatic and ground truth results was represented by the interval of the percentage difference between mean±1.96 SD. FIG. 11 shows example box-plots for end-systolic and end-diastolic areas for all four chambers.

The techniques disclosed herein can be implemented in various embodiments to perform fully automatic segmentation for all four chambers in echocardiograms simultaneously. In some embodiments, the adversarial training further improves segmentation performance. The accuracy of the automatic segmentation has been shown to be comparable to manual segmentation performed by board-certified cardiologists. Other conventional methods applied for segmentation of echocardiograms (e.g., 2D echocardiograms) either require user interaction and additional inputs (e.g., initial segmentation for a single frame or manually finding the chamber's center point) or rely on a certain ventricular shape prior to proceed the segmentation, setup the necessary parameters, or edit the obtained segmentation. None of these inputs or a priori knowledge are necessary using the techniques disclosed herein to perform segmentations of all four chambers at the same time.

Figure 12:
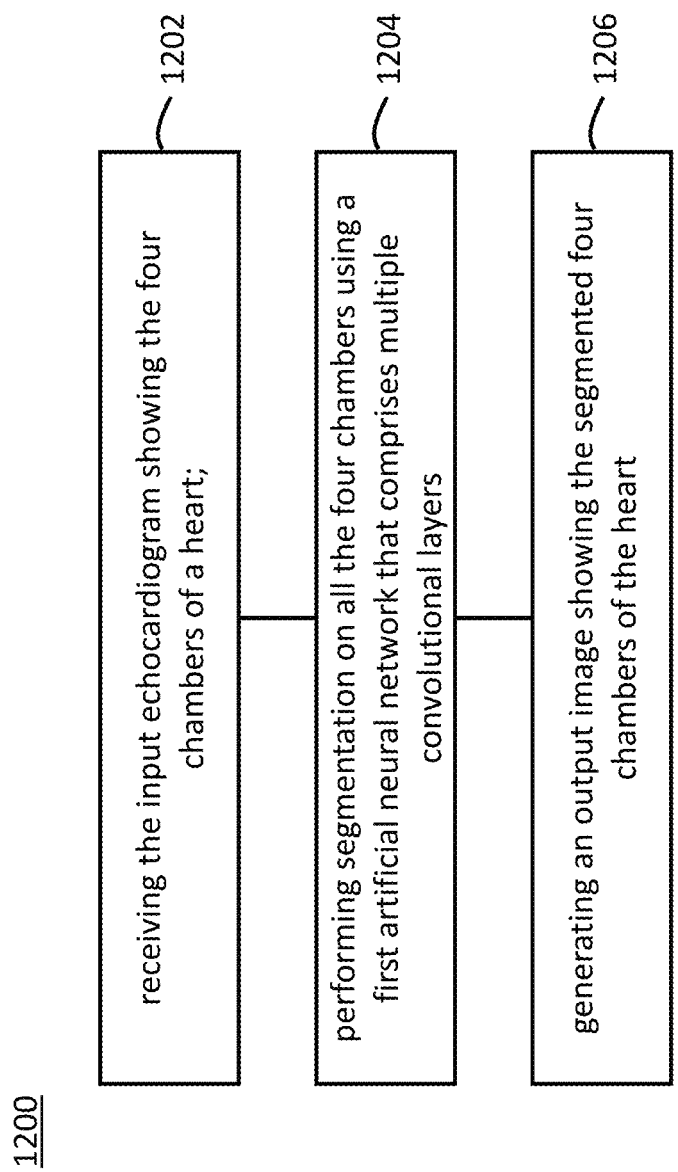
FIG. 12 is a flowchart representation of a method for segmenting four chambers of a heart in an input echocardiogram in accordance with the present technology.

In one example aspect, as shown in FIG. 12, a method 1200 for generating segmented image data based on an input echocardiogram comprises receiving an input echocardiogram that includes four chambers of a heart (1202), performing segmentation on all the four chambers simultaneously using a first artificial neural network that comprises multiple layers (1204), and generating an output image that includes the segmented four chambers of the heart by combining data from selected layers of the first artificial neural network (1206).

In some embodiments, the method includes obtaining weights from one or more pre-trained neural network models and initiating parameters for the first artificial neural network in part based on the obtained weights. In some embodiments, the method further includes tuning the first artificial neural network in part based on the obtained weights.

In some embodiments, the method includes generating an intermediate image that is smaller than the input echocardiogram and modifying the intermediate image by at least one of: randomly displacing a center of the intermediate image, zooming up the intermediate image, distorting a mean or a standard deviation of pixel values in the intermediate image, rotating the intermediate image, or adding noise to the intermediate image.

In some embodiments, the method includes generating, by a classification layer of the first artificial neural network, a probability map indicating a likelihood of a pixel being present in at least one of the four chambers. The method may further include determining, by a second artificial neural network based on the input echocardiogram and the probability map, whether the segmented four chambers correspond to a manually performed segmentation of the input echocardiogram.

In some embodiments, performing the segmentation comprises generating multiple convolved feature maps for identifying a left ventricle in the input echocardiogram, computing a region of interest around the identified left ventricle, and identifying a boundary of the identified left ventricle. In some embodiments, the first artificial neural network includes a convolutional neural network. In some embodiments, the second artificial neural network includes a convolutional neural network. The first and second artificial neural networks can both be fully-connected.

In some embodiments, the segmentation is performed without any user intervention. In some embodiments, the segmentation is performed without inputs or a priori knowledge of the four chambers, the inputs or a priori knowledge including at least one of: an initial segmentation of a single frame of the input echocardiogram, a center point of one of the four chambers, or a shape of either right or left ventricular of the four chambers.

In another example aspect, a segmentation system of echocardiogram images comprises a first artificial neural network configured to receive an input echocardiogram that includes four chambers of a heart. The first artificial neural network is configured to perform segmentation on all four chambers simultaneously to produce one or more probability maps for the four chambers, each of the one or more probability maps indicating a likelihood of a pixel being present in at least one of the four chambers. The system also comprises a second artificial neural network in communication with the first artificial neural network to receive the one or more probability maps and to determine whether a segmented chamber corresponds to a manually performed segmentation of the chamber.

In some embodiments, the first artificial neural network is configured to obtain weights from one or more pre-trained neural network models and initiate parameters in part based on the obtained weights. In some embodiments, the first artificial neural network is configured to generate an intermediate image that is smaller than the input echocardiogram and modifying the intermediate image by at least one of: randomly displacing a center of the intermediate image, zooming up the intermediate image, distorting a mean or a standard deviation of pixel values in the intermediate image, rotating the intermediate image, or adding noise to the intermediate image. In some embodiments, the first artificial neural network comprises multiple layers including a classification layer to generate the one or more probability maps. In some embodiments, the first and the second artificial neural network are fully connected convolutional neural networks.

Figure 14:
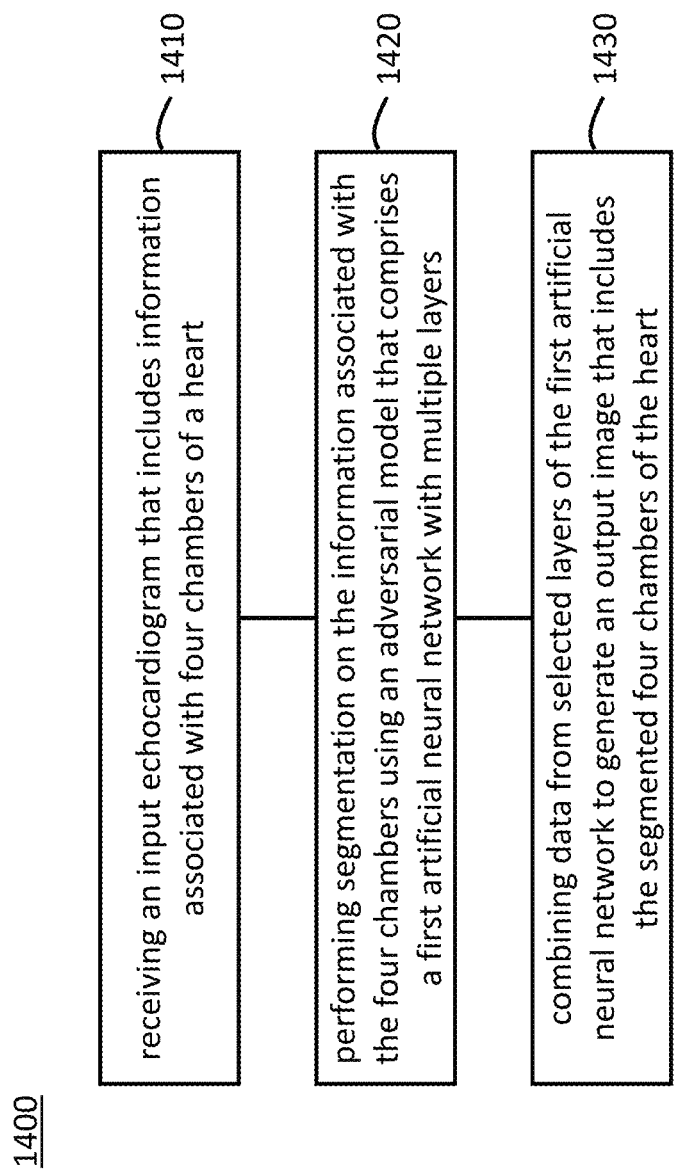
FIG. 14 is a flowchart representation of another method for segmenting four chambers of a heart in an input echocardiogram in accordance with the present technology.

In another example aspect, a method for generating segmented image data based on an input echocardiogram is disclosed. FIG. 14 is a flowchart representation of a method 1400 for segmenting four chambers of a heart in an input echocardiogram in accordance with the present technology. The method 1400 includes, at operation 1410, receiving an input echocardiogram that includes information associated with four chambers of a heart. The method 1400 includes, at operation 1420, performing segmentation on the information associated with the four chambers using an adversarial model that comprises a first artificial neural network with multiple layers. The method 1400 includes, at operation 1430, combining data from selected layers of the first artificial neural network to generate an output image that includes the segmented four chambers of the heart.

In some embodiments, the adversarial model is trained based on real-time data augmentation that includes generating data representative of an intermediate image that is smaller than a test echocardiogram, modifying the data representative of the intermediate image, generating, by a classification layer of the first artificial neural network, a probability map for the data representative of the intermediate image, the probability map indicating a likelihood of a pixel being present in at least one of the four chambers, and determining, by a second artificial neural network of the adversarial model based on the test echocardiogram and the probability map, whether the segmented four chambers correspond to a manually performed segmentation of the test echocardiogram. The modification of the data representative results in at least one of: randomly displacing a center of the intermediate image, zooming up the intermediate image, distorting a mean or a standard deviation of pixel values in the intermediate image, rotating the intermediate image, or adding noise to the intermediate image. In some embodiments, the first artificial neural network is implemented as a generator in a Generative Adversarial Network (GAN) and the second artificial neural network is implemented as a discriminator in the GAN such as shown in FIG. 3.

In some embodiments, training the first artificial neural network includes obtaining weights from one or more pre-trained neural network models, initializing parameters of the first artificial neural network in part based on the obtained weights, and tuning the first artificial neural network in part based on the obtained weights. In some embodiments, performing the segmentation includes generating multiple convolved feature maps for identifying a center location of a left ventricle in the input echocardiogram, computing a region of interest around the identified center location of the left ventricle, and identifying a boundary of the identified left ventricle.

In some embodiments, the first artificial neural network and the second artificial neural network are fully-connected convolutional neural networks. In some embodiments, the segmentation is performed without any human manipulation of the information associated with the four chambers. In some embodiments, the segmentation is performed without inputs or a priori knowledge of the four chambers. The inputs or a priori knowledge includes at least one of: an initial segmentation of a single frame of the input echocardiogram, a center point of one of the four chambers, or a shape of either right or left ventricular of the four chambers.

In another example aspect, a device for processing an input echocardiogram includes a processor, and a memory including processor executable code. The processor executable code upon execution by the processor configures the processor to receive an input echocardiogram that includes information associated with four chambers of a heart, perform segmentation on the information associated with the four chambers using an adversarial model that comprises a first artificial neural network with multiple layers, and combine data from selected layers of the first artificial neural network to generate an output image that includes the segmented four chambers of the heart.

In some embodiments, the processor is configured to trained the adversarial model based on generating data representative of an intermediate image that is smaller than a test echocardiogram, modifying the data representative of the intermediate image, generating, by a classification layer of the first artificial neural network, a probability map for the data representative of the intermediate image, the probability map indicating a likelihood of a pixel being present in at least one of the four chambers, and determining, by a second artificial neural network of the adversarial model based on the test echocardiogram and the probability map, whether the segmented four chambers correspond to a manually performed segmentation of the test echocardiogram. Modifying the data representative of the intermediate image results in at least one of: randomly displacing a center of the intermediate image, zooming up the intermediate image, distorting a mean or a standard deviation of pixel values in the intermediate image, rotating the intermediate image, or adding noise to the intermediate image. In some embodiments, the first artificial neural network is implemented as a generator in a Generative Adversarial Network (GAN) and the second artificial neural network is implemented as a discriminator in the GAN (e.g., as shown in FIG. 3).

In some embodiments, the processor is configured to train the first artificial neural network based on obtaining weights from one or more pre-trained neural network models, initializing parameters of the first artificial neural network in part based on the obtained weights, and tuning the first artificial neural network in part based on the obtained weights.

In some embodiments, the processor is configured to perform the segmentation based on generating multiple convolved feature maps for identifying a left ventricle in the input echocardiogram, computing a region of interest around the identified left ventricle, and identifying a boundary of the identified left ventricle.

In some embodiments, the first artificial neural network and the second artificial neural network are fully-connected convolutional neural networks. In some embodiments, the processor is configured to perform the segmentation without any human manipulation of the information associated with the four chambers. In some embodiments, the processor is configured to perform the segmentation without inputs or a priori knowledge of the four chambers. The inputs or a priori knowledge including at least one of: an initial segmentation of a single frame of the input echocardiogram, a center point of one of the four chambers, or a shape of either right or left ventricular of the four chambers.

In yet another example aspect, a system for segmenting echocardiogram images includes a first artificial neural network configured to receive an input echocardiogram that includes information associated with four chambers of a heart. The first artificial neural network is configured to perform segmentation on the information associated with the four chambers based on generating data representative of an intermediate image that is smaller than the input echocardiogram, modifying the data representative of the intermediate image, and generating one or more probability map based on the data representative of the intermediate image. Modifying the data representative results in at least one of: randomly displacing a center of the intermediate image, zooming up the intermediate image, distorting a mean or a standard deviation of pixel values in the intermediate image, rotating the intermediate image, or adding noise to the intermediate image. Each of the one or more probability maps indicates a likelihood of a pixel being present in at least one of the four chambers. The system also includes a second artificial neural network in communication with the first artificial neural network to receive the one or more probability maps and to determine whether a segmented chamber corresponds to a manually performed segmentation of the chamber.

In some embodiments, the first artificial neural network is trained based on obtaining weights from one or more pre-trained neural network models, initializing parameters of the first artificial neural network in part based on the obtained weights, and tuning the first artificial neural network in part based on the obtained weights. In some embodiments, the first artificial neural network is implemented as a generator in a Generative Adversarial Network (GAN) and the second artificial neural network is implemented as a discriminator in the GAN. In some embodiments, the first artificial neural network is configured to perform the segmentations without any human manipulation of the information associated with the four chambers or a priori knowledge of the four chambers.

At least parts of the disclosed embodiments (e.g., the neural networks) can be implemented in digital electronic circuitry, or in computer software, firmware, or hardware. For example, electronic circuits can be used to control the operation of the detector arrays and/or to process electronic signals that are produced by the detectors. At least some of those embodiments or operations can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Computer-readable media suitable for storing computer program instructions and data include all forms of non-volatile memory, media and memory devices, including, by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Figure 13:
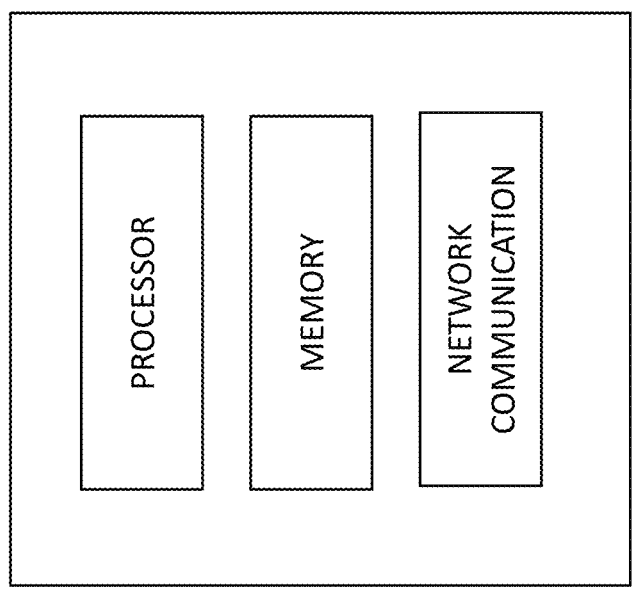
FIG. 13 is a diagrammatic representation of a machine in the example form of a computer system in accordance with the present technology.

FIG. 13 is a diagrammatic representation of a machine in the example form of a computer system 1300 within which a set of instructions, for causing the machine to perform any one or more of the methodologies or modules discussed herein, can be executed.

In the example of FIG. 13, the computer system 1300 includes a processor, memory, non-volatile memory, and a network communication interface device. Various common components (e.g., cache memory) are omitted for illustrative simplicity. The computer system 1300 is intended to illustrate a hardware device on which any of the components described in the example of FIGS. 1, 3-5 (and any other components described in this specification) can be implemented. The computer system 1300 can be of any applicable known or convenient type. The components of the computer system 1300 can be coupled together via a bus or through some other known or convenient device.

This disclosure contemplates the computer system 1300 taking any suitable physical form. As example and not by way of limitation, computer system 1000 can be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 1300 can include one or more computer systems 1300; be unitary or distributed; span multiple locations; span multiple machines; or reside in a cloud, which can include one or more cloud components in one or more networks. Where appropriate, one or more computer systems 1000 can perform without substantial spatial or temporal limitation one or more steps of one or more methods described or illustrated herein. As an example and not by way of limitation, one or more computer systems 1000 can perform in real time or in batch mode one or more steps of one or more methods described or illustrated herein. One or more computer systems 1300 can perform at different times or at different locations one or more steps of one or more methods described or illustrated herein, where appropriate.

The processor can be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 1000. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

The bus also couples the processor to the network interface device. The interface can include one or more of a modem or network interface. It will be appreciated that a modem or network interface can be considered to be part of the computer system 1300. The interface can include an analog modem, ISDN modem, cable modem, token ring interface, satellite transmission interface (e.g., "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 5 reside in the interface.

In operation, the computer system 1300 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

The invention claimed is:

1. A method for generating segmented image data based on an input echocardiogram, comprising:
    receiving the input echocardiogram that includes information associated with four chambers of a heart;
    performing segmentation on the information associated with the four chambers using an adversarial model that comprises a first artificial neural network with multiple layers; and
    combining data from selected layers of the first artificial neural network to generate an output image that includes the segmented four chambers of the heart,
    wherein the adversarial model is trained based on real-time data augmentation that includes:
    generating data representative of an intermediate image that is smaller than a test echocardiogram;
    modifying the data representative of the intermediate image that results in at least one of: randomly displacing a center of the intermediate image, zooming up the intermediate image, distorting a mean or a standard deviation of pixel values in the intermediate image, rotating the intermediate image, or adding noise to the intermediate image;
    generating, by a classification layer of the first artificial neural network, a probability map for the data representative of the intermediate image, the probability map indicating a likelihood of a pixel being present in at least one of the four chambers; and
    determining, by a second artificial neural network of the adversarial model based on the test echocardiogram and the probability map, whether the segmented four chambers correspond to a manually performed segmentation of the test echocardiogram.

2. The method of claim 1, wherein the first artificial neural network is implemented as a generator in a Generative Adversarial Network (GAN), and wherein the second artificial neural network is implemented as a discriminator in the GAN.

3. The method of claim 1, wherein training the first artificial neural network includes:
    obtaining weights from one or more pre-trained neural network models;
    initializing parameters of the first artificial neural network in part based on the obtained weights; and
    tuning the first artificial neural network in part based on the obtained weights.

4. The method of claim 1, wherein performing the segmentation comprises:
    generating multiple convolved feature maps for identifying a center location of a left ventricle in the input echocardiogram;
    computing a region of interest around the identified center location of the left ventricle; and
    identifying a boundary of the identified left ventricle.

5. The method of claim 1, wherein the first artificial neural network and the second artificial neural network are fully-connected convolutional neural networks.

6. The method of claim 1, wherein the segmentation is performed without any human manipulation of the information associated with the four chambers.

7. The method of claim 1, wherein the segmentation is performed without inputs or a priori knowledge of the four chambers, the inputs or a priori knowledge including at least one of: an initial segmentation of a single frame of the input echocardiogram, a center point of one of the four chambers, or a shape of either right or left ventricle of the four chambers.

8. A device for processing an input echocardiogram, comprising:
    a processor, and
    a memory including processor executable code, wherein the processor executable code upon execution by the processor configures the processor to:
    receive the input echocardiogram that includes information associated with four chambers of a heart;
    perform segmentation on the information associated with the four chambers using an adversarial model that comprises a first artificial neural network with multiple layers; and
    combine data from selected layers of the first artificial neural network to generate an output image that includes the segmented four chambers of the heart,
    wherein the processor is configured to train the adversarial model based on:
    generating data representative of an intermediate image that is smaller than a test echocardiogram;
    modifying the data representative of the intermediate image that results in at least one of: randomly displacing a center of the intermediate image, zooming up the intermediate image, distorting a mean or a standard deviation of pixel values in the intermediate image, rotating the intermediate image, or adding noise to the intermediate image;
    generating, by a classification layer of the first artificial neural network, a probability map for the data representative of the intermediate image, the probability map indicating a likelihood of a pixel being present in at least one of the four chambers; and
    determining, by a second artificial neural network of the adversarial model based on the test echocardiogram and the probability map, whether the segmented four chambers correspond to a manually performed segmentation of the test echocardiogram.

9. The device of claim 8, wherein the first artificial neural network is implemented as a generator in a Generative Adversarial Network (GAN), and wherein the second artificial neural network is implemented as a discriminator in the GAN.

10. The device of claim 8, wherein the processor is configured to train the first artificial neural network based on:
obtaining weights from one or more pre-trained neural network models;
initializing parameters of the first artificial neural network in part based on the obtained weights; and
tuning the first artificial neural network in part based on the obtained weights.

11. The device of claim 8, wherein the processor is configured to perform the segmentation based on:
generating multiple convolved feature maps for identifying a left ventricle in the input echocardiogram;
computing a region of interest around the identified left ventricle; and
identifying a boundary of the identified left ventricle.

12. The device of claim 8, wherein the first artificial neural network and the second artificial neural network are fully-connected convolutional neural networks.

13. The device of claim 8, wherein the processor is configured to perform the segmentation without any human manipulation of the information associated with the four chambers.

14. The device of claim 8, wherein the processor is configured to perform the segmentation without inputs or a priori knowledge of the four chambers, the inputs or a priori knowledge including at least one of: an initial segmentation of a single frame of the input echocardiogram, a center point of one of the four chambers, or a shape of either right or left ventricular of the four chambers.

15. A system for segmenting echocardiogram images, comprising:
a first artificial neural network configured to receive an input echocardiogram that includes information associated with four chambers of a heart, the first artificial neural network configured to perform segmentation on the information associated with the four chambers based on:
generating data representative of an intermediate image that is smaller than the input echocardiogram,
modifying the data representative of the intermediate image that results in at least one of: randomly displacing a center of the intermediate image, zooming up the intermediate image, distorting a mean or a standard deviation of pixel values in the intermediate image, rotating the intermediate image, or adding noise to the intermediate image, and
generating one or more probability maps based on the data representative of the intermediate image, each of the one or more probability maps indicating a likelihood of a pixel being present in at least one of the four chambers; and
a second artificial neural network in communication with the first artificial neural network to receive the one or more probability maps and to determine whether a segmented chamber corresponds to a manually performed segmentation of the chamber.

16. The system of claim 15, wherein the first artificial neural network is trained based on:
obtaining weights from one or more pre-trained neural network models;
initializing parameters of the first artificial neural network in part based on the obtained weights; and
tuning the first artificial neural network in part based on the obtained weights.

17. The system of claim 15, wherein the first artificial neural network is implemented as a generator in a Generative Adversarial Network (GAN), and wherein the second artificial neural network is implemented as a discriminator in the GAN.

18. The system of claim 15, wherein the first artificial neural network is configured to perform the segmentations without any human manipulation of the information associated with the four chambers or a priori knowledge of the four chambers.

* * * * *